(12) United States Patent
Saruwatari

(10) Patent No.: US 6,737,551 B2
(45) Date of Patent: May 18, 2004

(54) PROCESS FOR PRODUCING BISPHENOL A

(75) Inventor: Tetsuya Saruwatari, Yamaguchi (JP)

(73) Assignee: Idemitsu Petrochemical Co., Ltd., Tokyo (JP)

( * ) Notice: Subject to any disclaimer, the term of this patent is extended or adjusted under 35 U.S.C. 154(b) by 0 days.

(21) Appl. No.: 10/204,264

(22) PCT Filed: Dec. 17, 2001

(86) PCT No.: PCT/JP01/11037

§ 371 (c)(1),
(2), (4) Date: Aug. 20, 2002

(87) PCT Pub. No.: WO02/057206

PCT Pub. Date: Jul. 25, 2002

(65) Prior Publication Data

US 2003/0013927 A1 Jan. 16, 2003

(30) Foreign Application Priority Data

Jan. 19, 2001 (JP) .......................................... 2001-11971

(51) Int. Cl.$^7$ ............................................... C07C 39/16
(52) U.S. Cl. ........................................................ 568/728
(58) Field of Search .......................................... 568/728

(56) References Cited

U.S. PATENT DOCUMENTS 6,414,199 B1    7/2002    Saruwatari
6,429,343 B1  * 8/2002    Iwahara
6,486,222 B2  * 11/2002   Kissinger

FOREIGN PATENT DOCUMENTS

| EP | 1160229 | 12/2001 |
| JP | 11-246458 | 9/1999 |
| WO | WO-01/49640 | * 7/2001 |

* cited by examiner

Primary Examiner—Michael L. Shippen
(74) Attorney, Agent, or Firm—Oblon, Spivak, McClelland, Maier & Neustadt, P.C.

(57) ABSTRACT

In the production of bisphenol A by condensation of phenol and acetone with the use of a cation exchange resin as a catalyst and optionally a free mercaptan as a promoter, the degree of conversion of phenol is maintained by increasing the molar ration of acetone/phenol with the deterioration of the cation exchange resin; with this method, bisphenol A can be effectively produced with industrial advantage.

7 Claims, No Drawings

PROCESS FOR PRODUCING BISPHENOL A

TECHNICAL FIELD

The present invention relates to a method of producing bisphenol A [2,2-bis (4-hydroxyphenyl) propane]. More specifically, the present invention relates to a method of producing bisphenol A in which, in the production of bisphenol A from phenol and acetone with the use of a cation exchange resin as a catalyst and optionally a free mercaptan as a promoter, the degree of conversion of phenol is maintained by changing the reaction conditions with the deterioration of the catalyst, so that bisphenol A is effectively produced.

BACKGROUND OF THE INVENTION

Bisphenol A has been known as an important compound for raw material for engineering plastics, such as polycarbonate resins, polyacrylate resins, etc, or for epoxy resins, and the demand for it tends to be still more growing recently.

Bisphenol A is produced by the condensation of an excess of phenol and acetone in the presence of an acid catalyst and optionally a promoter, such as a sulfur compound, etc.

As the acid catalyst for that reaction, inorganic mineral acids, such as sulfuric acid, hydrochloric acid, etc. were conventionally used. However, cation exchange resins have recently attracted attention (GB Patent Nos. 842209, 849565 and 883391), and have come to be industrially used.

On the other hand, it has been known that as for sulfur compounds used as the promoter, alkyl mercaptans with or without substituting groups, such as methyl mercaptan, ethyl mercaptan, thioglycolic acid, etc., are useful (U.S. Pat. Nos. 2,359,242 and 2,775,620). The mercaptans function to increase the reaction rate and improve the selectivity. For example, as reaction by-products in the production of bisphenol A, 2-(2-hydroxyphenyl)-2-(4-hydroxyphenyl) propane (a combination of o- and p'-types) is mainly formed, and tris-phenol, polyphenol, etc. are also formed. Especially, in cases where bisphenol A is used as raw material for polycarbonate resins, polyacrylate resins, etc., required is colorless high purity bisphenol A containing a reduced amount of those by-products. To this end, mercaptans are used as a promoter in order not only to increase the reaction rate but also to suppress the formation of the by-products and increase the selectivity.

With respect to the reaction conditions (the temperature, the molar ration of acetone/phenol) at which phenol and acetone are condensed to produce bisphenol A, various considerations have been made. For example, Japanese Unexamined Patent Publication No. 54(1979)-19951 discloses a method in which the molar ratio between phenol and a carbonyl compound is set to be in the range of 10:1 to 30:1 and the reaction temperature is controlled to be in the range of 40–100° C.; Japanese Unexamined Patent Publication No. 54(1979)-19952 discloses a method in which the molar ratio between phenol and a carbonyl compound is set to be in the range of 3:1 to 50:1 and the reaction temperature is controlled to be in the range of 30–120° C.; and Japanese Patent Publication No. 63(1988)-52021 discloses a method in which an excess of phenol is used in an amount of moles four to ten times more than the mole(s) of acetone and the reaction is carried out at a temperature in the range of 40–100° C.

However, it is the fact that it has not heretofore been practiced to effectively change the reaction conditions with the deterioration of the cation exchange resin.

It has been known that the effect of the reaction temperature on the improvement in the degree of conversion of phenol is small in the reaction system in which the cation exchange resin is used as a catalyst and the mercaptan is used as a promoter. In addition, if one tries to deal with the deterioration of the catalyst through the reaction temperature, an undesirable situation results: specifically, rapid increase in the reaction temperature is inevitable. In this case, it is considered that elimination of sulfonic groups introduced in general cation exchange resins is promoted, which may adversely affect the quality of bisphenol A as the product.

Further, the reason why the degree of conversion of phenol is unlikely to be improved even if the reaction temperature is increased is deemed to be that in that system the diffusion of the raw material or the product within the gel structure of the cation exchange resin is the rate-determining factor of the reaction rate.

DISCLOSURE OF THE INVENTION

An object of the present invention is to provide an industrially useful method of producing bisphenol A in which, in the production of bisphenol A from phenol and acetone with the use of a cation exchange resin as a catalyst and optionally a mercaptan as a promoter, the degree of conversion of phenol is maintained by changing the reaction conditions with the deterioration of the catalyst, so that bisphenol A is effectively produced.

The inventors of the present invention have found, through extensive studies to achieve the above-mentioned object, that the degree of conversion of phenol can be effectively maintained and elimination of sulfonic groups from the cation exchange resin can be suppressed by increasing the molar ratio of acetone/phenol by not more than 1/20 at one time with the deterioration of the catalyst, whereby the above object can be achieved. The present invention has been made based on the above finding.

Specifically, the present invention provides a method of producing bisphenol A in which, in the production of bisphenol A by condensation of phenol and acetone with the use of a cation exchange resin as a catalyst, the degree of conversion of phenol is maintained by increasing the molar ratio of acetone/phenol by not more than 1/20 at one time with the deterioration of the catalyst.

BEST MODE FOR CARRYING OUT THE INVENTION

The method according to the present invention is a method of producing bisphenol A in which phenol and acetone are condensed with the use of a cation exchange resin as a catalyst and optionally a free mercaptan as a promoter. There is no specific limitation with respect to the kind of the cation exchange resin to be used, and any of those which are conventionally employed as catalysts for the production of bisphenol A can be used. However, sulfonic acid type cation exchange resins are preferred especially in terms of the catalytic activity.

There is no specific limitation with respect to the kind of the sulfonic acid type cation exchange resins to be used inasmuch as they are strong acidic cation exchange resins having sulfonic groups. Examples of the sulfonic acid type cation exchange resin include sulfonated styrene-divinyl benzene copolymer, sulfonated cross-linked styrene polymer, phenol formaldehyde-sulfonic acid resin, benzene formaldehyde-sulfonic acid resin, etc. These may be used singly or in combination.

The free mercaptan as the promoter as used herein means a compound having a free form of SH group in the molecule. As the free mercaptan, an alkyl mercaptan can be adopted, which may be either of a non-substituted alkyl mercaptan and a substituted alkyl mercaptan having at least one substituting group, such as a carboxylic group, an amino group, a hydroxyl group, etc. Examples of non-substituted mercaptans include methyl mercaptan, ethyl mercaptan, n-butyl mercaptan, n-octyl mercaptan, etc. Examples of the substituted alkyl mercaptan include mercaptocarboxylic acids such as thioglycolic acid, β-mercaptopropionic acid, etc., aminoalkane thiols such as 2-amino ethane thiol, 2,2-dimethyl thiazolidine, etc., mercaptoalcohols such as mercaptoethanol, etc. Among these, the non-substituted alkyl mercaptans are especially preferred in terms of the cocatalytic action. In addition, these mercaptans may be used singly or in combination.

The amount of each of these mercaptans is generally selected to be in the range of 0.1–20 mole %, preferably in the range of 1–10 mole %, relative to acetone, which is one of the raw materials to be used.

Further, there is no specific limitation with respect to the ratio of the amount between phenol and acetone, but it is desirable that the amount of unreacted acetone is as small as possible in terms of the easiness of purification of the produced bisphenol A and from an economical point of view. Therefore, it is advantageous that phenol is employed in an amount in excess of its stoichiometric amount. Generally, phenol is employed in an amount of 3–30 moles, preferably 5–15 moles, per one mole of acetone.

The method of producing bisphenol A according to the present invention does not generally require a reaction solvent except for the cases where the reaction is carried out at such low temperatures that the viscosity of the reaction liquid is too high or the reaction liquid solidifies resulting in difficulty in operation.

The condensation reaction between phenol and acetone in the present invention can be carried out in either of a batch-wise manner and a continuous manner. However, in terms of the production efficiency, preferred is a fixed bed continuous reaction system in which phenol, acetone and optionally above-explained free mercaptan are continuously fed to a reaction column packed with a cation exchange resin as an acid catalyst and are allowed to react. In this respect, the reaction can be carried out with one reaction column, but two or more reaction columns may be used so that they are arranged in series. It is industrially particularly advantageous to arrange two or more reaction columns each packed with the cation exchange resin in series and to use a fixed bed multiple stage continuous reaction system.

The reaction conditions for the fixed bed continuous reaction system will hereinbelow be explained.

The molar ratio of acetone/phenol in this reaction is generally selected to be in the range of 1/30 to 1/3, and preferably in the range of 1/15 to 1/5. If this molar ratio is lower than 1/30, there is a risk that the reaction rate becomes too low. If the molar ratio is greater than 1/3, more impurities are generated and the selectivity of bisphenol A tends to be lower.

Meanwhile, in cases where the free mercaptan is not immobilized on the cation exchange resin, the molar ratio of the free mercaptan/acetone is generally selected to be in the range of 0.1/100 to 20/100, and preferably in the range of 1/100 to 10/100. If this molar ratio is lower than 0.1/100, there is a risk that improvements with respect to the reaction rate and the selectivity of bisphenol A are not sufficiently obtained. If this molar ratio is greater than 20/100, advantages are not fully enjoyed relative to the amount of the free mercaptan used.

The reaction temperature is generally selected to be in the range of 40–150° C., and preferably in the range of 60–110° C. If the reaction temperature is lower than 40° C., the reaction rate becomes low and the viscosity of the reaction liquid becomes extremely high which may create a risk of solidification. If the reaction temperature exceeds 150° C., it becomes difficult to control the reaction, the selectivity of bisphenol A (a combination of p- and p'-types) is lowered, and the cation exchange resin as a catalyst may decompose or deteriorate. In addition, LHSV (Liquid Hourly Space Velocity) of the material mixture is generally selected to be in the range of 0.2 $hr^{-1}$ to 30 $hr^{-1}$, and preferably in the range of 0.5 $hr^{-1}$ to 10 $hr^{-1}$.

In this kind of condensation reaction between phenol and acetone, the cation exchange resin with which the reaction column is packed deteriorates with a lapse of a certain time period of operation, and consequently the degree of conversion of phenol is lowered. In the present invention, when the degree of conversion of phenol is lowered to some extent in that way, the molar ratio of acetone/phenol is first increased within the above-mentioned range by once to several hundred times, and preferably by once to two hundred times. The degree to which the molar ratio of acetone/phenol is increased is set to be such that the difference between the molar ratios before and after each increase at one time is in the range of not more than 1/20. If this degree exceeds 1/20, a side reaction may occur, so that the yield of bisphenol A may be lowered, and the rate of deterioration of the resin may be increased. For these reasons, the desirable degree to which the molar ratio of acetone/phenol is increased is such that the difference between the molar ratios before and after each increase at one time is in the range of not more than 1/20, and preferably in the range of 1/30 to 1/100.

Meanwhile, if only the reaction temperature is raised without increasing the molar ratio of acetone/phenol, the degree of conversion of phenol may not be improved to a considerable extent, and elimination of sulfonic groups from the cation exchange resin may be promoted.

In the method according to the present invention, the reaction mixture coming from the reaction column or columns is subjected to a post treatment in a conventional way, whereby bisphenol A is obtained.

Explaining an example of the post treatment, concentration is first carried out prior to crystallization. Although there is no specific limitation with respect to the conditions under which the concentration is carried out, the concentration is generally carried out under the conditions in which the temperature is in the range of 130° C. to 170° C. and the pressure is in the range of 13 kPa to 53 kPa. If the temperature is lower than 130° C., high vacuum is requires. If the temperature is higher than 170° C., more impurities are generated and color development is caused thereby. Further, it is advantageous that the concentration of bisphenol A in the concentrated residue ranges from 25 wt. % to 40 wt. %. If this concentration is less than 25 wt. %, the yield of bisphenol A is low. If this concentration exceed 40 wt. %, it becomes difficult to carry the slurry after the crystallization.

Crystallization of an addition product composed of bisphenol A and phenol from the concentrated residue is carried out by means of the vacuum cooling crystallization method in which cooling is performed using evaporation latent heat of water generally under reduced pressure. In the vacuum cooling crystallization method, water is added to the concentrated residue in an amount of 3–20 wt. %, and the crystallization treatment is carried out generally at a temperature of 40–70° C. and a pressure of 3–13 kPa. If the amount of water added is less than 3 wt. %, heat removing capability is insufficient, and if this amount exceeds 20 wt. %, dissolution loss of bisphenol A becomes large, both of which cases are not desirable. Further, if the temperature of the crystallization treatment is lower than 40° C., there is a risk of increase in the viscosity after the crystallization and occurrence of solidification. If the temperature of the crystallization treatment exceeds 70° C., dissolution loss of bisphenol A becomes larger. Both of these cases are not desirable.

Thereafter, the addition product composed of bisphenol A and phenol as thus obtained by way of the crystallization treatment is separated by a conventional method, and is then subjected to a washing treatment generally using phenol. After that, the washed addition product is subjected to a disassembly processing into bisphenol A and phenol. The temperature at which the disassembly processing is carried out is generally selected to be in the range of 130–200° C., and preferably in the range of 150–180° C. The pressure at which the disassembly processing is carried out is generally selected to be in the range of 3–20 kPa.

High quality bisphenol A can be obtained from the bisphenol A thus obtained from the disassembly processing through removing the residual phenol in the latter bisphenol A substantially completely by the steam striping method, etc.

EXAMPLES

The present invention will hereinbelow be described in further detail based on examples. However, the present invention is not limited to such examples in any way.

Example 1

Three cylindrical vessels each having an inner diameter of 10 mm and a length of 1500 mm were each packed with a cation exchange resin (sulfonated styrene-divinyl benzene copolymer available from Mitsubishi Chemical Corporation; Product Name: DIAION SK 104) in an amount of 140 milliliters. Then, phenol at a flow rate of 300 g/hr, acetone at a flow rate of 9.3 g/hr and ethyl mercaptan at a flow rate of 0.5 g/hr were continuously fed to this set of reaction columns, and were allowed to react at 75° C.

In this case, the molar ratio of acetone/phenol was 1/20.

After a lapse of 100 hours, the degree of conversion of phenol was 7.2% at that time, and the average degree of conversion of phenol during that period was 7.5%.

Then, the reaction was continued in such a manner that the rates of feeding phenol and acetone were changed so that the molar ratio of acetone/phenol was set to be 1/15 while LHSV was maintained to be 3 $hr^{-1}$.

After a lapse of 100 hours from the change in the reaction conditions, the degree of conversion of phenol was 10.0% at that time, and the average degree of conversion of phenol during that period was 10.5%.

Comparative Example 1

Phenol at a flow rate of 300 g/hr, acetone at a flow rate of 18.5 g/hr and ethyl mercaptan at a flow rate of 1.3 g/hr were continuously fed to the same set of reaction columns as in Example 1, and were allowed to react at 75° C.

In this case, the molar ratio of acetone/phenol was 1/10, and LHSV was 3 $hr^{-1}$.

After a lapse of 400 hours, the degree of conversion of phenol was 11% at that time, and the average degree of conversion of phenol during that period was 12%.

Then, the reaction was continued in such a manner that the rates of feeding phenol and acetone were changed so that the molar ratio of acetone/phenol was set to be 1/5 while LHSV was maintained to be 3 $hr^{-1}$.

After a lapse of 50 hours from the change in the reaction conditions, the degree of conversion of phenol was 8.2% at that time, and the average degree of conversion of phenol during that period was 9.5%.

INDUSTRIAL APPLICABILITY

According to the present invention, in the production of bisphenol A from phenol and acetone with the use of a cation exchange resin as a catalyst and optionally a free mercaptan as a promoter, the degree of conversion of phenol is maintained by changing the reaction conditions with the deterioration of the catalyst, so that bisphenol A can be effectively produced.

What is claimed is:

1. A method of producing bisphenol A in which, in the production of bisphenol A by condensation of phenol and acetone with the use of a cation exchange resin as a catalyst, the degree of conversion of phenol is maintained by increasing the molar ratio of acetone/phenol by 1/20 or less at one time with the deterioration of the cation exchange resin.

2. A method of producing bisphenol A according to claim 1, wherein the cation exchange resin is a sulfonic acid type cation exchange resin.

3. A method of producing bisphenol A according to claim 1, wherein a free mercaptan is used as a promoter, along with the use of the cation exchange resin as a catalyst.

4. A method of producing bisphenol A according to claim 3, wherein the free mercaptan is an alkyl mercaptan, mercaptocarboxylic acid, aminoalkane thiol or mercaptoalcohol.

5. A method of producing bisphenol A according to claim 1, wherein the molar ratio of acetone/phenol is in the range of 1/30–1/3.

6. A method of producing bisphenol A according to claim 3, wherein the molar ratio of the free mercaptan/acetone is in the range of 0.1/100–20/100.

7. A method of producing bisphenol A according to claim 1, wherein the condensation reaction is carried out at a temperature in the range of 40–150° C.

* * * * *